United States Patent
Wilson et al.

(10) Patent No.: US 6,482,634 B1
(45) Date of Patent: Nov. 19, 2002

(54) METHODS AND VECTOR CONSTRUCTS USEFUL FOR PRODUCTION OF RECOMBINANT AAV

(75) Inventors: James M. Wilson, Gladwyne, PA (US); Weidong Xiao, Jenkintown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/528,470

(22) Filed: Mar. 17, 2000

Related U.S. Application Data (63) Continuation of application No. PCT/US98/19479, filed on Sep. 18, 1998.
(60) Provisional application No. 60/059,330, filed on Sep. 19, 1997.

(51) Int. Cl.$^7$ .................................................. C12N 7/00
(52) U.S. Cl. .................... 435/235.1; 435/239; 435/325; 435/369; 435/320.1; 536/23.72; 536/24.1
(58) Field of Search ................................ 435/325, 366, 435/369, 235.1, 320.1, 239; 536/23.72, 24.1

(56) References Cited

U.S. PATENT DOCUMENTS

| | | | | |
|---|---|---|---|---|
| 5,622,856 A | * | 4/1997 | Natsoulis ................. | 435/320.1 |
| 5,658,776 A | | 8/1997 | Flotte et al. .............. | 435/172.3 |
| 6,027,931 A | | 2/2000 | Natsoulis et al. ......... | 435/235.1 |
| 6,274,354 B1 | * | 8/2001 | Wilson et al. ............ | 435/91.42 |

FOREIGN PATENT DOCUMENTS

| | | | | |
|---|---|---|---|---|
| WO | | 95/06743 | * 3/1995 | ........... C12N/15/86 |
| WO | WO 96/17947 | | 6/1996 | |
| WO | | 96/40240 | * 12/1996 | ......... A61K/39/325 |
| WO | WO 96/40955 | | 12/1996 | |
| WO | WO 97/06272 | | 2/1997 | |
| WO | WO 98/10086 | | 3/1998 | |
| WO | WO 98/46728 | | 10/1998 | |
| WO | WO 99/07833 | | 2/1999 | |
| WO | WO 99/15677 | | 4/1999 | |
| WO | WO 99/15685 | | 4/1999 | |

OTHER PUBLICATIONS

Li et al (Journal of Virology 71(7):5236–5243, Jul. 1997).*
B. J. Carter in "Handbook of Parvoviruses", ed., P. Tijssen, CRC Press, pp. 155–168 (1990).
R. Kotin, "Prospects for the Use of Adeno–Associated Virus as a Vector for Human Gene Therapy", *Hum. Gene Ther.,* 5:793–801 (Jul. 1994).
J.D. Watson et al., Molecular Biology of the Gene, The Benjamin/Cummings Publishing Company, Inc., 1987, XP002091111, pp. 703–705.
J. Sambrook et al., "Molecular Cloning. A Laboratory Manual", Cold Spring Harbour Laboratory Press, 1989, XP002091112, pp. 16.5–16.6.

* cited by examiner

*Primary Examiner*—Mary E. Mosher
(74) *Attorney, Agent, or Firm*—Howson and Howson (57) ABSTRACT

Methods for efficient production of recombinant AAV employ a host cell containing a first nucleic acid molecule comprising from 5' to 3', a parvovirus P5 promoter, a spacer, an AAV rep sequence and an AAV cap gene sequence, wherein said spacer is of sufficient size to reduce expression of the rep78 and rep68 gene products; a second nucleic acid molecule comprising a minigene comprising a transgene flanked by AAV inverse terminal repeats (ITRs) and under the control of regulatory sequences directing expression thereof in a host cell; and helper functions essential to the replication and packaging of rAAV, which functions are not provided by the first or second nucleic acid molecules. Host cells and molecule constructs are also described.

56 Claims, 2 Drawing Sheets

SEQUENCE LISTING

<160> NUMBER OF SEQ ID NOS: 5

<210> SEQ ID NO 1
<211> LENGTH: 8509
<212> TYPE: DNA
<213> ORGANISM: Artificial Sequence
<220> FEATURE:
<223> OTHER INFORMATION: Description of Artificial Sequence: Recombinant
      plasmid containing adeno-associated virus
      sequences, CMV promoter and lacZ gene

<400> SEQUENCE: 1
gcccaatacg caaaccgcct ctccccgcgc gttggccgat tcattaatgc agctgcgcgc      60
tcgctcgctc actgaggccg cccgggcaaa gcccgggcgt cgggcgacct ttggtcgccc     120
ggcctcagtg agcgagcgag cgcgcagaga gggagtggcc aactccatca ctaggggttc     180
cttgtagtta atgattaacc cgccatgcta cttatctacg tagccattct ctagccctg      240 caggtcgtta cataacttac ggtaaatggc ccgcctggct gaccgcccaa cgacccccgc     300

-continued

| | | |
|---|---|---|
| ccattgacgt caataatgac gtatgttccc atagtaacgc caatagggac tttccattga | 360 |
| cgtcaatggg tggagtattt acggtaaact gcccacttgg cagtacatca agtgtatcat | 420 |
| atgccaagta cgcccctat tgacgtcaat gacggtaaat ggcccgcctg gcattatgcc | 480 |
| cagtacatga ccttatggga ctttcctact tggcagtaca tctacgtatt agtcatcgct | 540 |
| attaccatgg tgatgcggtt ttggcagtac atcaatgggc gtggatagcg gtttgactca | 600 |
| cggggatttc caagtctcca ccccattgac gtcaatggga gtttgttttg gcaccaaaat | 660 |
| caacgggact ttccaaaatg tcgtaacaac tccgccccat tgacgcaaat gggcggtagg | 720 |
| cgtgtacggt gggaggtcta taagcaga gctcgtttag tgaaccgtca gatcgcctgg | 780 |
| agacgccatc cacgctgttt tgacctccat agaagacacc gggaccgatc cagcctccgg | 840 |
| actctagagg atccggtact cgaggaactg aaaaaccaga aagttaactg gtaagtttag | 900 |
| tcttttttgtc ttttatttca ggtcccggat ccggtggtgg tgcaaatcaa agaactgctc | 960 |
| ctcagtggat gttgccttta cttctaggcc tgtacgaag tgttacttct gctctaaaag | 1020 |
| ctgcggaatt gtacccgcgg ccgcaattcc cgggatcga aagagcctgc taaagcaaaa | 1080 |
| aagaagtcac catgtcgttt actttgacca acaagaacgt gattttcgtt gccggtctgg | 1140 |
| gaggcattgg tctggacacc agcaaggagc tgctcaagcg cgatcccgtc gttttacaac | 1200 |
| gtcgtgactg ggaaaaccct ggcgttaccc aacttaatcg ccttgcagca catccccctt | 1260 |
| tcgccagctg gcgtaatagc gaagaggccc gcaccgatcg cccttcccaa cagttgcgca | 1320 |
| gcctgaatgg cgaatggcgc tttgcctggt ttccggcacc agaagcggtg ccggaaagct | 1380 |
| ggctggagtg cgatcttcct gaggccgata ctgtcgtcgt cccctcaaac tggcagatgc | 1440 |
| acggttacga tgcgcccatc tacaccaacg taacctatcc cattacggtc aatccgccgt | 1500 |
| ttgttcccac ggagaatccg acgggttgtt actcgctcac atttaatgtt gatgaaagct | 1560 |
| ggctacagga aggccagacg cgaattattt ttgatgcgt taactcggcg tttcatctgt | 1620 |
| ggtgcaacgg gcgctgggtc ggttacggcc aggacagtcg tttgccgtct gaatttgacc | 1680 |
| tgagcgcatt tttacgcgcc ggagaaaacc gcctcgcgt gatggtgctg cgttggagtg | 1740 |
| acggcagtta tctggaagat caggatatgt ggcggatgag cggcattttc cgtgacgtct | 1800 |
| cgttgctgca taaaccgact acacaaatca gcgatttcca tgttgccact cgctttaatg | 1860 |
| atgatttcag ccgcgctgta ctggaggctg aagttcagat gtgcggcgag ttgcgtgact | 1920 |
| acctacgggt aacagtttct ttatggcagg gtgaaacgca ggtcgccagc ggcaccgcgc | 1980 |
| cttttcggcgg tgaaattatc gatgagcgtg gtggttatgc cgatcgcgtc acactacgtc | 2040 |
| tgaacgtcga aaacccgaaa ctgtggagcg ccgaaatccc gaatctctat cgtgcggtgg | 2100 |
| ttgaactgca caccgccgac ggcacgctga ttgaagcaga agcctgcgat gtcggttttcc | 2160 |
| gcgaggtgcg gattgaaaat ggtctgctgc tgctgaacgg caagccgttg ctgattcgag | 2220 |
| gcgttaaccg tcacgagcat catcctctgc atggtcaggt catggatgag cagacgatgg | 2280 |
| tgcaggatat cctgctgatg aagcagaaca actttaacgc cgtgcgctgt tcgcattatc | 2340 |
| cgaaccatcc gctgtggtac acgctgtgcg accgctacgg cctgtatgtg gtggatgaag | 2400 |
| ccaatattga aacccacggc atggtgccaa tgaatcgtct gaccgatgat ccgcgctggc | 2460 |
| taccggcgat gagcgaacgc gtaacgcgaa tggtgcagcg cgatcgtaat cacccgagtg | 2520 |
| tgatcatctg gtcgctgggg aatgaatcag gccacggcgc taatcacgac gcgctgtatc | 2580 |
| gctggatcaa atctgtcgat ccttcccgcc cggtgcagta tgaaggcggc ggagccgaca | 2640 |
| ccacggccac cgatattatt tgcccgatgt acgcgcgcgt ggatgaagac cagcccttcc | 2700 |

```
cggctgtgcc gaaatggtcc atcaaaaaat ggctttcgct acctggagag acgcgcccgc    2760
tgatcctttg cgaatacgcc cacgcgatgg gtaacagtct tggcggtttc gctaaatact    2820
ggcaggcgtt tcgtcagtat ccccgtttac agggcggctt cgtctgggac tgggtggatc    2880
agtcgctgat taaatatgat gaaaacggca acccgtggtc ggcttacggc ggtgattttg    2940
gcgatacgcc gaacgatcgc cagttctgta tgaacgtctc ggtctttgcc gaccgcacgc    3000
cgcatccagc gctgacggaa gcaaaacacc agcagcagtt tttccagttc cgtttatccg    3060
ggcaaaccat cgaagtgacc agcgaatacc tgttccgtca tagcgataac gagctcctgc    3120
actggatggt ggcgctggat ggtaagccgc tggcaagcgg tgaagtgcct ctggatgtcg    3180
ctccacaagg taaacagttg attgaactgc ctgaactacc gcagccggag agcgccgggc    3240
aactctggct cacagtacgc gtagtgcaac cgaacgcgac cgcatggtca gaagccgggc    3300
acatcagcgc ctggcagcag tggcgtctgg cggaaaacct cagtgtgacg ctccccgccg    3360
cgtcccacgc catcccgcat ctgaccacca gcgaaatgga ttttttgcatc gagctgggta    3420 ataagcgttg gcaatttaac cgccagtcag gctttctttc acagatgtgg attggcgata    3480
aaaaacaact gctgacgccg ctgcgcgatc agttcacccg tgcaccgctg gataacgaca    3540
ttggcgtaag tgaagcgacc cgcattgacc ctaacgcctg ggtcgaacgc tggaaggcgg    3600
cgggccatta ccaggccgaa gcagcgttgt tgcagtgcac ggcagataca cttgctgatg    3660
cggtgctgat tacgaccgct cacgcgtggc agcatcaggg gaaaacctta tttatcagcc    3720
ggaaaaccta ccggattgat ggtagtggtc aaatggcgat taccgttgat gttgaagtgg    3780
cgagcgatac accgcatccg gcgcggattg gcctgaactg ccagctggcg caggtagcag    3840
agcgggtaaa ctggctcgga ttagggccgc aagaaaacta tcccgaccgc cttactgccg    3900
cctgttttga ccgctgggat ctgccattgt cagacatgta taccccgtac gtcttcccga    3960
gcgaaaacgg tctgcgctgc gggacgcgcg aattgaatta tggcccacac cagtggcgcg    4020
gcgacttcca gttcaacatc agccgctaca gtcaacagca actgatggaa accagccatc    4080
gccatctgct gcacgcggaa gaaggcacat ggctgaatat cgacggtttc catatgggga    4140
ttggtggcga cgactcctgg agcccgtcag tatcggcgga attacagctg agcgccggtc    4200
gctaccatta ccagttggtc tggtgtcaaa ataataata accgggcagg ccatgtctgc    4260
ccgtatttcg cgtaaggaaa tccattatgt actatttaaa aaacacaaac ttttggatgt    4320
tcggtttatt ctttttcttt tacttttta tcatgggagc ctacttcccg tttttcccga    4380
tttggctaca tgcatcaac catatcagca aaagtgatac gggtattatt tttgccgcta    4440
tttctctgtt ctcgctatta ttccaaccgc tgtttggtct gctttctgac aaactcggcc    4500
tcgactctag gcggccgcgg ggatccagat atgataagat acattgatga gtttggacaa    4560
accacaacta gaatgcagtg aaaaaaatgc tttatttgtg aaatttgtga tgctattgct    4620
ttatttgtaa ccattataag ctgcaataaa caagttaaca acaacaattg cattcatttt    4680
atgtttcagg ttcaggggga ggtgtgggag gttttttcgg atcctctaga gtcgacctgc    4740
aggggctaga atggctacgt agataagtag catggcgggt taatcattaa ctacaaggaa    4800
cccctagtga tggagttggc cactccctct ctgcgcgctc gctcgctcac tgaggccggg    4860
cgaccaaagg tcgcccgacg cccgggcttt gcccggcgg cctcagtgag cgagcgagcg    4920
cgcagctggc gtaatagcga agaggcccgc accgatcgcc cttcccaaca gttgcgcagc    4980
ctgaatggcg aatggaattc cagacgattg agcgtcaaaa tgtaggtatt tccatgagcg    5040
```

-continued

```
tttttcctgt tgcaatggct ggcggtaata ttgttctgga tattaccagc aaggccgata    5100
gtttgagttc ttctactcag gcaagtgatg ttattactaa tcaaagaagt attgcgacaa    5160
cggttaattt gcgtgatgga cagactcttt tactcggtgg cctcactgat tataaaaaca    5220
cttctcagga ttctggcgta ccgttcctgt ctaaaatccc tttaatcggc ctcctgttta    5280
gctcccgctc tgattctaac gaggaaagca cgttatacgt gctcgtcaaa gcaaccatag    5340
tacgcgccct gtagcggcgc attaagcgcg gcgggtgtgg tggttacgcg cagcgtgacc    5400
gctacacttg ccagcgccct agcgcccgct cctttcgctt tcttcccttc ctttctcgcc    5460
acgttcgccg gctttccccg tcaagctcta aatcgggggc tccctttagg gttccgattt    5520
agtgctttac ggcacctcga cccccaaaaa cttgattagg gtgatggttc acgtagtggg    5580
ccatcgccct gatagacggt ttttcgccct ttgacgttgg agtccacgtt ctttaatagt    5640
ggactcttgt tccaaactgg aacaacactc aaccctatct cggtctattc ttttgattta    5700
taagggattt tgccgatttc ggcctattgg ttaaaaaatg agctgattta acaaaaattt    5760
aacgcgaatt ttaacaaaat attaacgttt acaatttaaa tatttgctta tacaatcttc    5820 ctgttttttgg ggcttttctg attatcaacc ggggtacata tgattgacat gctagtttta    5880
cgattaccgt tcatcgattc tcttgtttgc tccagactct caggcaatga cctgatagcc    5940
tttgtagaga cctctcaaaa atagctaccc tctccggcat gaatttatca gctagaacgg    6000
ttgaatatca tattgatggt gatttgactg tctccggcct ttctcacccg tttgaatctt    6060
tacctacaca ttactcaggc attgcattta aaatatatga gggttctaaa aatttttatc    6120
cttgcgttga aataaaggct tctcccgcaa aagtattaca gggtcataat gttttttggta    6180 caaccgattt agctttatgc tctgaggctt tattgcttaa ttttgctaat tctttgcctt    6240
gcctgtatga tttattggat gttggaattc ctgatgcggt attttctcct tacgcatctg    6300
tgcggtattt cacaccgcat atggtgcact ctcagtacaa tctgctctga tgccgcatag    6360
ttaagccagc cccgacaccc gccaacaccc gctgacgcgc cctgacgggc ttgtctgctc    6420
ccggcatccg cttacagaca agctgtgacc gtctccggga gctgcatgtg tcagaggttt    6480
tcaccgtcat caccgaaacg cgcgagacga agggcctcg tgatacgcct atttttatag    6540
gttaatgtca tgataataat ggtttcttag acgtcaggtg gcacttttcg gggaaatgtg    6600
cgcggaaccc ctatttgttt atttttctaa atacattcaa atatgtatcc gctcatgaga    6660
caataaccct gataaatgct tcaataatat tgaaaaagga agagtatgag tattcaacat    6720
ttccgtgtcg cccttattcc cttttttgcg gcattttgcc ttcctgtttt tgctcaccca    6780
gaaacgctgg tgaaagtaaa agatgctgaa gatcagttgg gtgcacgagt gggttacatc    6840
gaactggatc tcaacagcgg taagatcctt gagagttttc gccccgaaga acgttttcca    6900
atgatgagca cttttaaagt tctgctatgt ggcgcggtat tatcccgtat tgacgccggg    6960
caagagcaac tcggtcgccg catacactat tctcagaatg acttggttga gtactcacca    7020
gtcacagaaa agcatcttac ggatggcatg acagtaagag aattatgcag tgctgccata    7080
accatgagtg ataacactgc ggccaactta cttctgacaa cgatcggagg accgaaggag    7140
ctaaccgctt ttttgcacaa catgggggat catgtaactc gccttgatcg ttgggaaccg    7200
gagctgaatg aagccatacc aaacgacgag cgtgacacca cgatgcctgt agcaatggca    7260
acaacgttgc gcaaactatt aactggcgaa ctacttactc tagcttcccg gcaacaatta    7320
atagactgga tggaggcgga taaagttgca ggaccacttc tgcgctcggc ccttccggct    7380
ggctggttta ttgctgataa atctggagcc ggtgagcgtg gtctcgcgg tatcattgca    7440
```

```
gcactggggc cagatggtaa gccctcccgt atcgtagtta tctacacgac ggggagtcag    7500
gcaactatgg atgaacgaaa tagacagatc gctgagatag gtgcctcact gattaagcat    7560
tggtaactgt cagaccaagt ttactcatat atactttaga ttgatttaaa acttcatttt    7620
taatttaaaa ggatctaggt gaagatcctt tttgataatc tcatgaccaa aatcccttaa    7680
cgtgagtttt cgttccactg agcgtcagac cccgtagaaa agatcaaagg atcttcttga    7740
gatccttttt ttctgcgcgt aatctgctgc ttgcaaacaa aaaaaccacc gctaccagcg    7800
gtggtttgtt tgccggatca agagctacca actcttttc cgaaggtaac tggcttcagc    7860
agagcgcaga taccaaatac tgtccttcta gtgtagccgt agttaggcca ccacttcaag    7920
aactctgtag caccgcctac atacctcgct ctgctaatcc tgttaccagt ggctgctgcc    7980
agtggcgata gtcgtgtct taccggttg gactcaagac gatagttacc ggataaggcg    8040
cagcggtcgg gctgaacggg gggttcgtgc acacagccca gcttggagcg aacgacctac    8100
accgaactga gatacctaca gcgtgagcta tgagaaagcg ccacgcttcc cgaagggaga    8160
aaggcggaca ggtatccggt aagcggcagg gtcggaacag gagagcgcac gagggagctt    8220
ccagggggaa acgcctggta tctttatagt cctgtcgggt ttcgccacct ctgacttgag    8280
cgtcgatttt tgtgatgctc gtcagggggg cggagcctat ggaaaaacgc cagcaacgcg    8340
gcctttttac ggttcctggc cttttgctgg cctttgctc acatgttctt tcctgcgtta    8400
tcccctgatt ctgtggataa ccgtattacc gcctttgagt gagctgatac cgctcgccgc    8460
agccgaacga ccgagcgcag cgagtcagtg agcgaggaag cggaagagc              8509

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 2
tgtagttaat gattaacccg ccatgctact tatc                                34

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 3
ggcggctgcg cgttcaaacc tcccgcttca aaatg                               35

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 4
tatttaagcc cgagtgagct                                                20

<210> SEQ ID NO 5
<211> LENGTH: 28
<212> TYPE: DNA
<213> ORGANISM: Artificial Sequence
<220> FEATURE:
```

```
<223> OTHER INFORMATION: Description of Artificial Sequence:  PCR primer

<400> SEQUENCE: 5
tagcatggcg ggttaatcat taactaca                                              28
```

METHODS AND VECTOR CONSTRUCTS USEFUL FOR PRODUCTION OF RECOMBINANT AAV

CROSS-REFERENCE TO RELATED APPLICATIONS

This is a continuation of International Patent Application No. PCT/US98/19479, filed on Sep. 18, 1998, which claims the benefit of the priority of U.S. Patent Application No. 60/059,330, filed on Sep. 19, 1997.

This invention was made with financial assistance from the National Institutes of Health Grant No. NIAMS P01AR/MS43648. The United States government has certain rights in this invention.

BACKGROUND OF THE INVENTION

Adeno-associated virus (AAV) is a replication-deficient parvovirus, the genome of which is about 4.6 kb in length, including 145 bp inverted terminal repeats (ITRs). Two open reading frames encode a series of rep and cap polypeptides. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are the 145 bp ITRs, the first 125 bp of which are capable of forming Y- or T-shaped duplex structures. Of importance for the development of AAV vectors, the entire rep and cap domains can be excised and replaced with a therapeutic or reporter transgene [B. J. Carter, in "Handbook of Parvoviruses", ed., P. Tijsser, CRC Press, pp.155–168 (1990)]. It has been shown that the ITRs represent the minimal sequence required for replication, rescue, packaging, and integration of the AAV genome.

When this nonpathogenic human virus infects a human cell, the viral genome integrates into chromosome 19 resulting in latent infection of the cell. Production of infectious virus and replication of the virus does not occur unless the cell is coinfected with a lytic helper virus, such as adenovirus or herpesvirus. Upon infection with a helper virus, the AAV provirus is rescued and amplified, and both AAV and helper virus are produced. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ss DNA genomes following cell lysis.

AAV possesses unique features that make it attractive as a vector for delivering foreign DNA to cells. Various groups have studied the potential use of AAV in the treatment of disease states; however, progress towards establishing AAV as a transducing vector for gene therapy has been slow for a variety of reasons. One obstacle to the use of AAV for delivery of DNA is lack of highly efficient schemes for encapsidation of recombinant genomes and production of infectious virions [See, R. Kotin, Hum. Gene Ther., 5:793–801 (1994)].

One proposed solution involves transfecting the recombinant adeno-associated virus (rAAV) containing the transgene into host cells followed by co-infection with wild-type AAV and adenovirus. However, this method leads to unacceptably high levels of wild-type AAV. Incubation of cells with rAAV in the absence of contaminating wild-type AAV or helper adenovirus is associated with little recombinant gene expression. In the absence of rep, integration is inefficient and not directed to chromosome 19.

A widely recognized means for manufacturing transducing AAV virions entails co-transfection with two different, yet complementing plasmids. One of these contains the therapeutic or reporter transgene sandwiched between the two cis acting AAV ITRs. The AAV components that are needed for rescue and subsequent packaging of progeny recombinant genomes are provided in trans by a second plasmid encoding the viral open reading frames for rep and cap proteins. However, both rep and cap are toxic to the host cells. This toxicity has been the major source of difficulty in providing these genes in trans for the construction of a useful rAAV gene therapy vector.

Other methods have been proposed to enable high titer production of rAAV. For example, U.S. Pat. No. 5,658,776 refers to packaging systems and processes for packaging AAV vectors that replace the AAV P5 promoter with a heterologous promoter. Alternatively, U.S. Pat. No. 5,622,856 refers to constructs and methods for AAV vector production, which provide constructs formed by moving the homologous P5 promoter to a position 3' to the rep genes, and optionally flanking the rep-cap and repositioned P5 promoter with FRT sequences.

There remains a need in the art for additional methods permitting the efficient production of AAV and recombinant AAV viruses for use in research and therapy.

SUMMARY OF THE INVENTION

The present invention provides novel methods, host cells, and vector constructs which permit efficient production of rAAV, by decreasing the expression of the rep78/rep68 gene products, while leaving the expression of rep52, rep40 and AAV structural proteins at a normal level.

In one aspect, the invention provides a host cell containing
  (a) a first nucleic acid molecule comprising from 5' to 3', a parvovirus P5 promoter, a spacer, an AAV rep sequence and an AAV cap sequence, wherein the spacer is of sufficient size to reduce expression of the rep78 and rep68 gene products;
  (b) a second nucleic acid molecule comprising a minigene comprising a transgene flanked by AAV inverse terminal repeats (ITRs) and under the control of regulatory sequences directing expression thereof in a host cell; and
  (c) helper functions essential to the replication and packaging of rAAV.

In another aspect, the invention provides a nucleic acid molecule useful in the production of recombinant AAV comprising from 5' to 3', a homologous P5 promoter, a spacer, an AAV rep sequence and an AAV cap sequence, wherein the spacer is of sufficient size to reduce, but not eliminate, expression of the rep78 and rep68 gene products.

In yet a further aspect, the invention provides a method for increasing the production of recombinant adeno-associated virus (rAAV) by culturing a host cell as described above, by which the rep78/rep68 gene products are reduced in expression, and isolating from the cell lysate or cell culture, high levels of recombinant AAV capable of expressing said transgene.

Other aspects and advantages of the present invention are described further in the following detailed description of the preferred embodiments thereof.

DETAILED DESCRIPTION OF THE INVENTION

The invention provides methods and compositions for efficiently producing high titers of rAAV. The method of this invention may be employed to produce rAAV carrying therapeutic transgenes, which are particularly useful in transferring the transgene to a host cell or tissue. These rAAV are also useful as research reagents, or as tools for the recombinant production of a transgene product in vitro.

I. Compositions

In one embodiment, the invention provides a host cell which contains the following components:

(a) a first nucleic acid molecule comprising from 5' to 3', a parvovirus P5 promoter, a spacer, an AAV rep gene sequence and an AAV cap gene sequence, wherein the spacer is of sufficient size to reduce expression of the rep78 and rep68 gene products relative to other rep gene products;

(b) a second nucleic acid molecule comprising a minigene comprising a transgene flanked by AAV inverted terminal repeats (ITRs) and under the control of regulatory sequences directing expression thereof in a host cell; and (c) helper functions essential to the replication and packaging of rAAV.

A. The First Nucleic Acid Molecule

The key components of the first molecule are arranged in 5' to 3' order: the parvovirus P5 promoter, a spacer interposed between the promoter and the start site of the rep gene sequence, and the cap gene sequence.

The parvovirus P5 promoter used in the first nucleic acid molecule is preferably homologous to the AAV serotype which provides the rep gene sequences and cap gene sequences. Alternatively, the promoter may be a P5 promoter from another AAV type than that which provides the rep and cap sequences. The AAV P5 promoter sequences, as well as the ITR sequences employed in the second nucleic acid molecule described below, may be obtained from any known AAV, including presently identified human AAV types. Similarly, AAVs known to infect other animals may also provide the P5 promoter, rep and cap gene sequences, and ITRs employed in the constructs of this invention. The selection of the AAV to provide any of these sequences is not anticipated to limit the following invention. For example, the P5 promoter may be provided by AAV type 1, AAV type 2, AAV type 3, AAV type 4, AAV type 5, parvovirus type H1, MVM, LuIII, or from any other parvovirus or AAV serotype. A variety of AAV strains are available from the American Type Culture Collection or are available by request from a variety of commercial and institutional sources. In the following exemplary embodiments an AAV-2 is used for convenience.

The spacer is a DNA sequence interposed between the promoter and the rep gene ATG (start) site. The spacer may have any desired design; that is, it may be a random sequence of nucleotides, or alternatively, may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or coding sequences with transcriptional controls. As illustrated below, two exemplary sources of spacer sequence are the λ phage ladder sequences or yeast ladder sequences, which are available commercially, e.g., from Gibco or Boehringer Mannheim, among others.

The spacer may be of any size sufficient to reduce expression of the rep78 and rep68 gene products, leaving the rep52, rep40 and cap gene products to be expressed at normal levels. The length of the spacer may therefore range from about 10 bp to about 10.0 kbp. As illustrated below spacers of 100 bp to about 8.0 kbp in length were used effectively. In one experimental design, maximum expression levels of rep78 and rep68 were achieved with a spacer of about 500 bp in length. Desirably, to reduce the possibility of recombination, the spacer is preferably less than 2 kbp in length. However, the invention is not so limited. The rep gene sequences and cap gene sequences are obtained from the same or a different serotype of AAV from that which supplies the P5 promoter. These sequences may be contiguous, or may be non-contiguous sequences, as desired, and may be derived from a single AAV or from different AAV sources. The AAV rep and cap sequences, as well as the P5 promoter may be obtained by conventional means (see Example 1 below). In all cases, in the first nucleic acid molecule, the P5 promoter and spacer are 5' to the rep cap sequences.

The first nucleic acid molecule may be in any form which transfers these components to the host cell. As one example, the first nucleic acid molecule is preferably in the form of a plasmid, which may contain other non-viral or viral sequences. However, this molecule does not contain the AAV ITRs and generally does not contain the AAV packaging sequences. As one example, the first nucleic acid molecule described in Example 1 below contains a plasmid sequence from the commercially available Bluescript plasmid. A series of such plasmids are identified by the designation pJWX-Y, with Y indicating a different size of spacer. As another example, a plasmid may contain the key components described above, and further contain adenovirus sequences, such as map units 0–1 and 9–16 thereof as well as plasmid sequence. This plasmid is desirably constructed so that it may be stably transfected into a cell.

Alternatively, the first nucleic acid molecule may be in the form of a recombinant virus, such as an adenovirus or baculovirus. For example, the key components may be inserted as a "minigene" into the E1 region of an E1-deleted adenovirus vector. See, e.g., published PCT patent application Nos. WO96/13598; WO96/13597 and U.S. Pat. No. 5,652,224, among others.

The first nucleic acid molecule may also exist in the host cell as an episome. Still alternatively, the molecule, or at least the key components described in detail below, may be integrated into the chromosome of the host cell. The methods employed for constructing a molecule of this invention are conventional genetic engineering or recombinant engineering techniques such as those described in conventional texts. See, e.g., Sambrook et al, Molecular Cloning. A Laboratory Manual. 2d edition, Cold Spring Harbor Laboratory, Cold Spring Harbor, N.Y. (1989). While Example 1 provides a specific illustration of the first nucleic acid molecule of this invention, using the information provided herein, one of skill in the art may select and design other suitable first nucleic acid molecules, with the choice of spacers, P5 promoters and the like, taking into consideration such factors as length, the presence of at least one set of translational start and stop signals, and optionally, the presence of polyadenylation sites.

B. The Second Nucleic Acid Molecule

The second nucleic acid molecule provides in cis a minigene, which is defined sequences which comprise a selected desired transgene, a promoter, and other regulatory elements necessary for expression of the transgene in a host cell, flanked by AAV inverse terminal repeats (ITRs).

The AAV sequences employed are preferably the cis-acting 5' and 3' inverted terminal repeat (ITR) sequences [See, e.g., B. J. Carter, in "Handbook of Parvoviruses", ed., P. Tijsser, CRC Press, pp.155–168 (1990)]. The ITR sequences are about 145 bp in length. Preferably, substantially the entire sequences encoding the ITRs are used in the vectors, although some degree of minor modification of these sequences is permissible for this use. The ability to modify these ITR sequences is within the skill of the art. [See, e.g., texts such as Sambrook et al, "Molecular Cloning. A Laboratory Manual.", 2d edit., Cold Spring Harbor Laboratory, New York (1989); Carter et al, cited above; and K. Fisher et al., *J. Virol.,* 70:520–532 (1996). As described above, the AAV source of such sequences is not a limitation upon this invention.

In one embodiment, the 5' and 3' AAV ITR sequences flank the selected transgene sequence and associated regulatory elements (i.e., the 5' AAV ITR is 5' of the transgene and the regulatory elements and the 3' AAV ITR is 3' of the transgene and regulatory elements). The transgene sequence of the second molecule is a nucleic acid sequence, heterologous to the AAV sequence, which encodes a polypeptide or protein of interest. The composition of the transgene sequence depends upon the use to which the resulting second molecule is to be put. For example, one type of transgene sequence includes a reporter sequence, which upon expression produces a detectable signal. Such reporter sequences include without limitation an *E. coli* beta-galactosidase (LacZ) cDNA, an alkaline phosphatase gene and a green fluorescent protein gene. These sequences, when associated with regulatory elements which drive their expression, provide signals detectable by conventional means, e.g., ultraviolet wavelength absorbance, visible color change, etc. For example, where the transgene is the LacZ gene, the presence of rAAV is detected by assays for beta-galactosidase activity.

However, desirably, the second molecule carries a non-marker gene which can be delivered to an animal via the rAAV produced by this method. A preferred type of transgene sequence is a therapeutic gene which expresses a desired gene product in a host cell. These therapeutic nucleic acid sequences typically encode products which, upon expression, are able to correct or complement an inherited or non-inherited genetic defect or treat an epigenetic disorder or disease. However, the selected transgene may encode any product desirable for study. The selection of the transgene sequence is not a limitation of this invention.

In addition to the major elements identified above, the minigene of the second molecule also includes conventional regulatory elements necessary to drive expression of the transgene in a cell transfected with this vector. Thus, the minigene comprises a selected promoter which is operatively linked to the transgene and located, with the transgene, between the AAV ITR sequences. Selection of the promoter used to drive expression of the transgene is a routine matter and is not a limitation of the vector.

In a preferred embodiment, the transgene is under the control of a cytomegalovirus (CMV) immediate early promoter/enhancer [see, e.g., Boshart et al, *Cell,* 41:521–530 (1985)]. However, other suitable promoters may be readily selected by one of skill in the art. Useful promoters may be constitutive promoters or regulated (inducible) promoters, which will enable control of expression of the transgene product. Another suitable promoter is the Rous sarcoma virus LTR promoter/enhancer. Still other promoter/enhancer sequences may be selected by one of skill in the art.

The minigene also desirably contains heterologous nucleic acid sequences including sequences providing signals required for efficient polyadenylation of the transcript and introns with functional splice donor and acceptor sites. A common poly-A sequence which is employed in the exemplary vectors of this invention is that derived from the papovavirus SV-40. The poly-A sequence generally is inserted following the transgene sequences and before the 3' AAV ITR sequence. A common intron sequence is also derived from SV-40, and is referred to as the SV-40 T intron sequence. A minigene of the present invention may also contain such an intron, desirably located between the promoter/enhancer sequence and the transgene. Selection of these and other common vector elements are conventional and many such sequences are available [see, e.g., Sambrook et al, and references cited therein].

The second nucleic acid molecule carrying the AAV ITRs flanking the minigene may be in any form which transfers these components to the host cell. As described above for the first nucleic acid molecule, the second molecule may contain a plasmid backbone. For example, the second nucleic acid molecule of Example 2 is in the form of a plasmid containing other viral or non-viral sequences. The plasmid may further contain adenovirus sequences, such as map units 0–1 and 9–16.

Alternatively, the second nucleic acid molecule may be in the form of a recombinant virus which is used to infect the host cell. The second molecule may be a recombinant replication-defective adenovirus containing the transgene operatively linked to expression control sequences in the region of an adenovirus E1 deletion. Suitable Ad/AAV recombinant viruses may be produced in accordance with known techniques. See, e.g., International patent applications WO96/13598, published May 9, 1996; WO 95/23867 published Sep. 8, 1995, and WO 95/06743 published Mar. 9, 1995, which are incorporated by reference herein.

As either a plasmid or a virus, the second nucleic acid molecule may exist in the host cell as an episome or may be integrated into the chromosome of the host cell.

The methods useful for constructing a second nucleic acid molecule of this invention are well-known to those of skill in the art and include genetic engineering, recombinant engineering, and synthetic techniques. See, e.g., Sambrook et al, cited above; and the international patent publications cited above.

C. Helper functions

Helper functions essential to the replication and packaging of rAAV are also provided by or to the host cell in a variety of ways. For example, essential helper functions may be provided by the molecules (a) and (b) which contain, for example, adenovirus gene sequences, as described above. As another example, at least one of the molecules (a) or (b) may be a recombinant virus, which also supplies some or all helper functions to the cell.

Alternatively, helper functions may be provided by the host cell by virtue of sequences integrated into the chromosome of the cell. For example, the host cell may be an adenovirus or herpesvirus packaging cell, i.e., it expresses adenovirus or herpesvirus proteins useful for the production of AAV, such as HEK 293 cells and other packaging cells. In the case where the helper functions are expressed by the selected host cell, or by the host cell transfected with (a) or (b), no additional molecules are required.

However, where a packaging cell line is not used as the host cell, or the helper functions are not sufficiently present, still another source of helper functions is a third nucleic acid molecule. In one embodiment this third nucleic acid molecule is a plasmid which contains helper functions. See, for example, the "helper" plasmids of FIG. 2A and FIG. 2B, which contain adenovirus sequences in a plasmid backbone.

In another embodiment, the third molecule is a recombinant or wild-type helper virus, such as an adenovirus, baculovirus, retrovirus or herpesvirus, which provides the helper functions. Whether the optional third molecule is a plasmid or virus, it may exist in the cell as an episome. Where the helper functions are available on a separate molecule, the "host cell" may be any mammalian cell and not necessarily a packaging cell, such as HEK 293. Examples of suitable parental host cell lines include, without limitation, HeLa, A549, KB, Detroit, and WI-38 cells. These cell lines are all available from the American Type Culture Collection, 10801 University Boulevard, Manassa, Va. 20110-2209. Other suitable parent cell lines may be obtained from other sources.

Examples 1–3 below illustrate useful molecules and host cells of this invention. Using the information provided herein and known techniques, one of skill in the art could readily construct a different recombinant virus (i.e., non-adenovirus) or a plasmid molecule which is capable of driving expression of the selected component in the host cell. For example, although less preferred because of their inability to infect non-dividing cells, vectors carrying the required elements of the first or second nucleic acid molecules, e.g., the P5-spacer-rep-cap or the ITR-transgene-ITR sequences, may be readily constructed using e.g., retroviruses or baculoviruses. Therefore, this invention is not limited by the virus or plasmid selected for purposes of introducing the essential elements of the first nucleic acid sequence or second nucleic acid sequence or the optional third nucleic acid sequence into the host cell.

II. Methods of the Invention

In another embodiment, the present invention provides a method for increasing the production of rAAV by decreasing the expression of the rep78 and rep68 gene products, keeping the expression of rep52 and rep40, and the cap gene products at normal levels. This method includes the steps of culturing a host cell described above, which contains nucleic acid molecules (a) and (b), and helper functions (c), as described above; and isolating from the cell lysate or cell culture, a recombinant AAV capable of expressing the transgene of molecule (b).

In one embodiment of the method, a selected host cell is co-transfected with the first and second nucleic acid molecules, as described above, and then infected with a wild-type (wt) or replication defective virus, or transfected helper plasmid, to supply the helper functions. Suitable helper viruses may be readily selected by those of skill in the art and include, for example, wt Ad2, wt Ad5, and herpesviruses, as well as the replication defective adenovirus dl309. Suitable helper plasmids may also be readily selected by those of skill in the art and include, for example, the pFG140, pFΔ13, and pBHG10, which are described herein. In another embodiment, the host cell is an adenovirus packaging cell, such as HEK 293, and the first or second nucleic acid molecule is a recombinant virus, which also contains the remaining adenovirus helper functions necessary to package AAV in the presence of the essential elements provided by (b) and (c). Selection of the means by which the helper functions are provided is not a limitation on the present invention.

Suitable techniques for introducing the molecules of this invention into the host cell are known to those of skill in the art. When all molecules or vectors are present in a cell and the cell is provided with helper functions, the rAAV is efficiently produced.

In another embodiment of the method of this invention, a packaging cell line is constructed which stably expresses the helper functions (c), or which expresses the first nucleic molecule (a). According to this aspect of the method, the cell line expressing the (c) or (a) elements can be substituted for the vector or plasmid (a) or (c) as described above. Thus, only the second molecule (i.e., the cis plasmid) described above is subsequently introduced into the cell.

Having obtained such a helper-expressing cell line, this cell line can be infected (or transfected) with the first vector (a) containing the rep and cap genes and the second vector (b) containing the minigene described above.

The methods of this invention demonstrate that the limiting step for the high yield of rAAV is not the replication of cis plasmid; but the packaging process and rep78 and rep68 can interfere with the packaging process directly or indirectly.

III. Production of Vectors and rAAV

Assembly of the selected DNA sequences contained within each of the molecules described above may be accomplished utilizing conventional techniques. Such techniques include cDNA cloning such as those described in texts [Sambrook et al, cited above], use of overlapping oligonucleotide sequences of the adenovirus, AAV genome combined with polymerase chain reaction, synthetic methods, and any other suitable methods which provide the desired nucleotide sequence.

Introduction of the molecules (as plasmids or viruses) into the host cell may also be accomplished using techniques known to the skilled artisan. Where appropriate, standard transfection and co-transfection techniques may be employed, e.g., $CaPO_4$ transfection or electoporation using the human embryonic kidney (HEK) 293 cell line (a human kidney cell line containing a functional adenovirus E1a gene which provides a transacting E1a protein). Other conventional methods employed in this invention include homologous recombination of the viral genomes, plaquing of viruses in agar overlay, methods of measuring signal generation, and the like.

Following infection/transfection, the host cell is then cultured to enable production of the rAAV [See, e.g., F. L. Graham and L. Prevec, *Methods Mol. Biol.*, 7:109–128 (1991), incorporated by reference herein]. Desirably, once the rAAV is identified, it may be recovered and purified using standard techniques.

The following examples illustrate the preferred methods of the invention. These examples are illustrative only and are not intended to limit the scope of the invention.

EXAMPLE 1
Construction of First Nucleic Acid Molecules
A. Trans Plasmids An exemplary first molecule of the present invention is provided as a plasmid containing the P5—spacer—AAV rep and cap genes as follows. See FIGS. 1A and 1B.

The AAV P5 promoter was amplified from the 121 bp XbaI-BamHI fragment from plasmid psub201, which contains the entire AAV2 genome [R. J. Samulski et al, *J. Virol.*, 61:3096–3101 (1987)] by PCR using two oligonucleotides:

oligo 1: TGT AGT TAA TGA TTA ACC CGC CAT GCT ACT TAT C [SEQ ID NO: 2] and oligo 2: GGC GGC TGC GCG TTC AAA CCT CCC GCT TCA AAA TG [SEQ ID NO: 3]. This P5 promoter sequence was subsequently cloned into plasmid pCR2.1 (Invitrogen), resulting in a new plasmid, pCR-P5. The AAV rep and cap coding region is amplified from the AAV type 2 virus by primers TATTTAAGCCCGAGTGAGCT [SEQ ID NO: 4] and TAGCATGGCGGGTTAATCAT-TAACTACA [SEQ ID NO: 5] and cloned into the unique SmaI site of pBluescript (Promega). The resulting plasmid is called pBS-AAV.

The P5 promoter is then excised from pCR-P5 by digestion with BamHI and XhoI, filled in by Klenow and then cloned into the ClaI site of plasmid pBS-AAV. The resulting plasmid, designated as P5-X, contains a unique EcoRV site between the P5 promoter and the initiation codon of rep78.

Figure 1A:
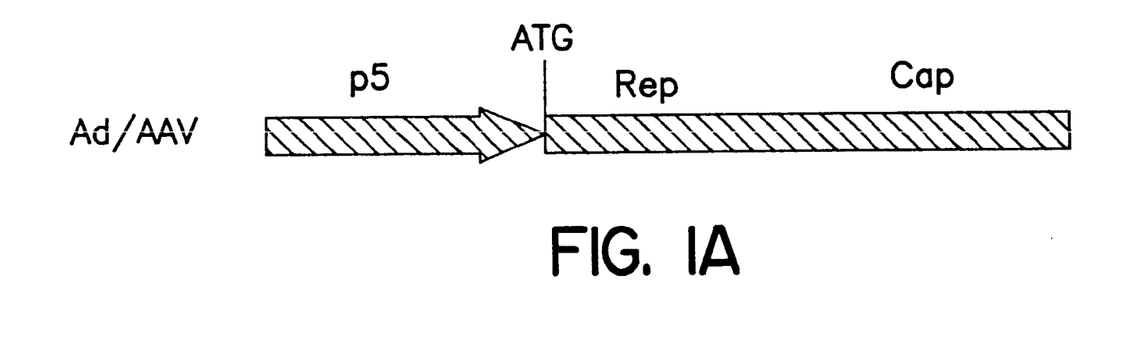
FIG. 1A is a schematic illustration of a naturally occurring AAV nucleic acid sequence illustrating the P5 promoter 5' to the start site (ATG) of the rep and cap gene sequences.
Figure 1B:
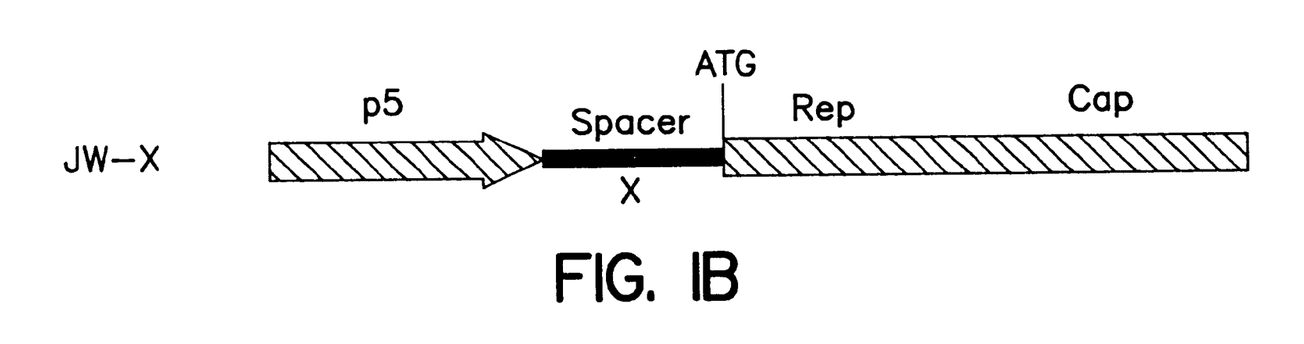
FIG. 1B is a schematic illustration of a first nucleic acid sequence of the present invention showing spacer 'X' inserted between the P5 promoter and the start site of rep and cap gene sequences.

The helper plasmid (i.e., first nucleic acid molecule) is made by cloning the desired spacer, in this case, either the λ phage or yeast 100 bp ladder and 500 bp ladder sequences (Gibco; BRL) into the EcoRV site in P5-X. The resulting series of plasmids are designated as pJWX-Y (FIG. 1A). Reference to Table I codifies these plasmids as pJWX-Y, in which Y indicates the size of the plasmid. The spacer sizes present in these plasmids range from 100 bp to 8 kb. FIG. 1A represents the normal relationship of P5 to the rep and cap genes. FIG. 1B represents the P5-spacer-rep-cap configuration of the first nucleic molecule.

EXAMPLE 2
Construction of Second Nucleic Acid Molecule

A "cis" plasmid, or second nucleic acid molecule useful in the present invention contains a minigene comprising AAV ITRs flanking a promoter and transgene, the minigene inserted into a plasmid backbone. In the present example, the exemplary cis plasmid is AV.CMVLacZ [SEQ ID NO: 1; see International Patent Application NO. WO95/13598] was utilized as the cis plasmid (the second nucleic acid molecule) useful in the methods of this invention. It is a rAAV cassette in which AAV rep and cap genes are replaced with a minigene expressing β-galactosidase from a CMV promoter. The linear arrangement of pAV.CMVLacZ includes:

(a) the 5' AAV ITR (bp 1–173) obtained by PCR using pAV2 [C. A. Laughlin et al, *Gene*, 23: 65–73 (1983)] as template [nucleotide numbers 365–538 of SEQ ID NO: 1];

(b) a CMV immediate early enhancer/promoter [Boshart et al, *Cell*, 41:521–530 (1985); nucleotide numbers 563–1157 of SEQ ID NO:1], (c) an SV40 intron (nucleotide numbers 1178–1179 of SEQ ID NO:1), (d) *E. coli* beta-galactosidase cDNA (nucleotide numbers 1356–4827 of SEQ ID NO:1), (e) an SV40 polyadenylation signal (a 237 BamHI-BclI restriction fragment containing the cleavage/poly-A signals from both the early and late transcription units; nucleotide numbers 4839–5037 of SEQ ID NO:1) and (f) 3'AAV ITR, obtained from pAV2 as a SnaBI-BglII fragment (nucleotide numbers 5053–5221 of SEQ ID NO:1). The remainder of the plasmid is simply plasmid backbone from a pBR322-derivative.

EXAMPLE 3
Production of rAAV

According to one embodiment of the present invention, $5 \times 10^6$ HEK 293 cells (American Type Culture Collection, Rockville, Md.) were transfected as follows: 2 μg of the helper plasmid pFΔ13 (FIG. 2B), 1 μg cis plasmid (pAV.CMVLacZ [SEQ ID NO: 1] of Example 2) and 1 μg of a trans plasmid selected from the groups listed in Table I, were transfected into 293 cells using DOTAP (Boehringer Mannheim Biotech).

Forty-eight hours later, each group of cells were harvested [J. Price et al, *Proc. Natl. Acad. Sci. USA*, 84:156–160 (1987)]. The cell lysate was then subjected to three rounds of freeze-thaw cycles. The amount of rAAV virus in supernatant was then titer by x-gal assay. To get pure rAAV virus, the cell lysate can be purified by CsCl gradient.

Table I lists the identity of the first nucleic acid molecule (i.e., the trans plasmid), the size of the spacer therein, and the total yield of rAAV from $2 \times 10^7$ cells in two production experiments was reported as LacZ-forming units (LFU). In Table I below 1 unit represent $1 \times 10^5$ LFU. In this case, pAdAAV represents a helper plasmid containing no spacer between P5 and repcap (see FIG. 1A).

TABLE I

| | | Total Yield | | |
|---|---|---|---|---|
| pTrans plasmid | Spacer | 1st | 2nd | Avg. |
| pAdAAV | none | 0.6 | 2.6 | 1.6 |
| pJWX-100 | 100 bp | 1 | 8.7 | 4.9 |
| pJWX-200 | 2 × 100 bp repeats | 22 | 33.4 | 28 |
| pJWX-300 | 3 × 100 bp repeats | 25 | 70 | 48 |
| pJWX-400 | 4 × 100 bp repeats | 29 | 60 | 45 |
| pJWX-500 | 5 × 100 bp repeats | 24 | 55 | 40 |
| pJWX-600 | 6 × 100 bp repeats | 31 | 130 | 81 |
| pJWX-700 | 7 × 100 bp repeats | 26 | 31.4 | 29 |
| pJWX-800 | 8 × 100 bp repeats | 29 | 28.3 | 29 |
| pJWX-900 | 9 × 100 bp repeats | N/A | 24 | 24 |
| pJWX-1k | 10 × 100 bp repeats | N/A | 33 | 33 |
| pJWX-1.1k | 11 × 100 bp repeats | 15 | 29 | 22 |
| pJWX-0.5k | 500 bp insert | 30 | 72 | 51 |
| pJWX-1k | 1 kb insert | 25 | 40 | 33 |
| pJWX-1.5k | 1.5 kb insert | 16 | 19 | 18 |
| pJWX-2k | 2 kb insert | 20 | 21 | 21 |
| pJWX-2.5k | 2.5 kb insert | 19 | 32 | 26 |
| pJWX-3k | 3.02 kb insert | 20 | 17 | 19 |
| pJWX-3.5k | 3.5 kb insert | 21 | 18.4 | 20 |
| pJWX-4k | 4.01 kb insert | 26 | 12.7 | 19 |
| pJWX-4.5k | 4.5 kb insert | 16 | 25 | 21 |
| pJWX-5k | 5.01 kb insert | 25 | 13.2 | 19 |
| pJWX-8k | 8 kb insert | 27 | 17.4 | 22 |

Surprisingly the rAAV yield is greatly improved using these helper plasmids.

EXAMPLE 4
Further Characterization of the rAAV Produced by the Method
A. Western Blots A Western blot was performed on transfections using a variety of different trans plasmids having different spacer sequences (Example 3). The results showed that the expression of rep78 and rep68 from these rAAV was greatly reduced while the expression of rep52, rep40 and AAV structural proteins remained unchanged. The results showed that replication of the gene containing cis plasmid was not significantly affected even though the amount of rep78 and rep68 was decreased.

Therefore, the optimization of rep78 and rep68 expression is critical for high titer rAAV production.

B. Southern Blot

A Southern blot was performed on transfections using the method of this invention using as "trans" plasmids or first nucleic acid molecules, either mock (no trans plasmid), AdAAV (a plasmid containing no spacer between the P5 and rep ATG site), or trans plasmids of the present invention containing varying sizes of spacer.

The position of the dimer and monomer bands did not change across all trans plasmids used. This demonstrates that the spacers between the P5 promoter and rep and cap genes of the trans plasmids of the invention do not affect the replication of the cis plasmid in the method. The AAV rep78/68 expression is sufficient in the method of this invention to maintain normal AAV replication.

EXAMPLE 5

Titer Comparisons

Figure 2A:
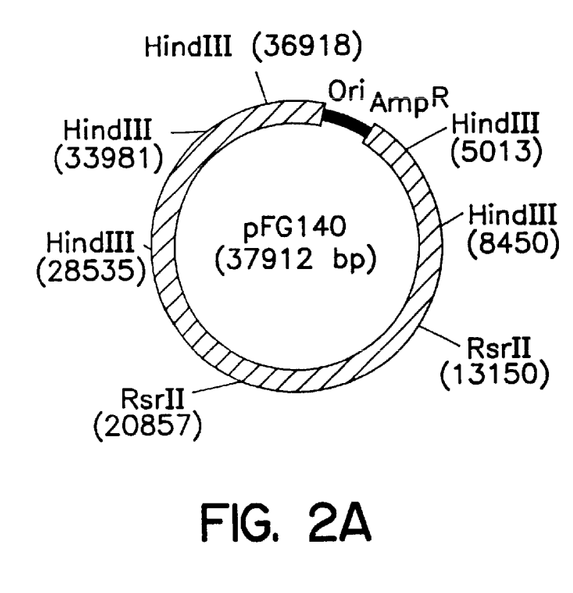
FIG. 2A is a schematic of plasmid pFG140, a commercially available (Microbix Biosystems, Inc.) plasmid containing a substantial portion of the adenovirus type 5 genome except for the E1a and E1b genes. This plasmid may be used to provide helper functions in the method of the invention.
Figure 2B:
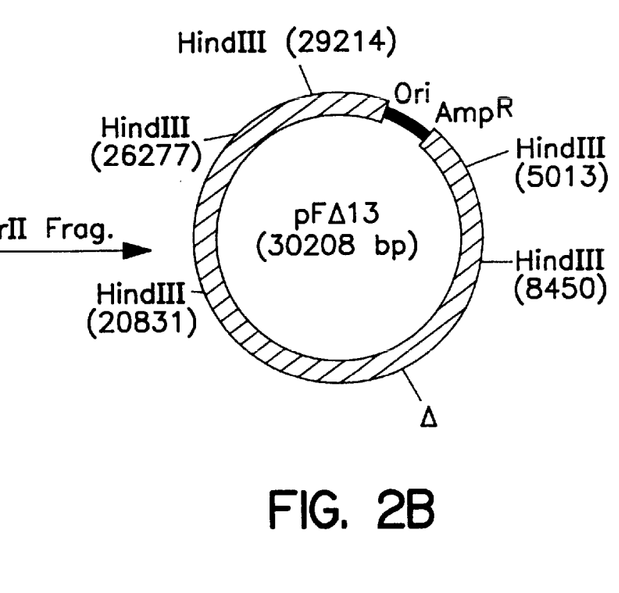
FIG. 2B is a schematic of a smaller plasmid pFΔ13, obtained by digesting pFG140 with RsrII, removing the smaller RsrII fragment and religating the plasmid. This plasmid may also be used to provide helper functions in the method of the invention.

The following two tables of data represent studies in which the methods of the present invention were performed by, (a) transfecting 293 cells by calcium phosphate precipitation with the trans plasmids identified in each table, the cis plasmid of Example 2 and the pFΔ13 helper plasmid of FIG. 2A or (b) transfecting $5 \times 10^6$ HEK 293 cells (American Type Culture Collection, Manassas, Va.) with 1 μg cis plasmid (pAV.CMVLacZ [SEQ ID NO: 1] of Example 2) and 1 μg of a trans plasmid selected from the groups listed in Table III using Lipofectin (Gibco BRL). These cells were thereafter infected with wildtype adenovirus type 5 at an MOI of 5 to supply the helper functions.

Table II illustrates the virus titers of three trials using protocol (a).

TABLE II

| Trans Plasmid | Trial 1 | Trial 2 | Trial 3 |
|---|---|---|---|
| Mock (no trans) | 0 | 0 | 0 |
| AdAAV (no spacer) | 100 | 100 | 100 |
| pJWX-23 | 693 | 391 | 838 |
| pJWX-4k | 344 | 330 | 444 |
| pJWX-1k | 441 | 321 | 475 |
| pJWX-500 | 344 | 278 | 437 |

Table III illustrates the titers of one trial using protocol (b). In this case a titer unit of 1 is equivalent to $3 \times 10^6$ infectious particles.

TABLE III

| Trans plasmid | Titer |
|---|---|
| Mock | 0.0 |
| AdAAV | 0.9 |
| pJWX-100 | 3.4 |
| pJWX-200 | 2.4 |
| pJWX-300 | 5.4 |
| pJWX-400 | 3.9 |
| pJWX-500 | 7.2 |
| pJWX-600 | 3.6 |
| pJWX-700 | 2.3 |
| pJWX-800 | 3.0 |
| pJWX-900 | 3.6 |
| pJWX-1k | 2.5 |
| pJWX-1.5k | 1.0 |
| pJWX-2k | 2.0 |

Publications cited in this specification are incorporated herein by reference. Numerous modifications and variations of the present invention are included in the above-identified specification and are expected to be obvious to one of skill in the art. Such modifications and alterations to the processes of the present invention are believed to be encompassed in the scope of the claims appended hereto.

What is claimed is:

1. A recombinant host cell containing
   (a) a first nucleic acid molecule comprising, from 5' to 3', a parvovirus P5 promoter, a spacer, an AAV rep gene sequence comprising a start site and encoding rep78, rep68, and other rep gene products, and an AAV a gene sequence, wherein said spacer consists of sequence heterologous to said promoter and the AAV rep gene sequence and said spacer is interposed between said promoter and the start site of the rep gene, such that said spacer is upstream of the AAV rep start site and is of sufficient size to reduce expression of the rep78 and rep68 gene products relative to other rep gene products, and
   (b) a second nucleic acid molecule comprising a minigene comprising a transgene flanked by AAV inverted terminal repeats (ITRs) and under the control of regulatory sequences directing expression thereof in a host cell; and
   (c) helper functions essential to the replication and packaging of rAAV.

2. The cell according to claim 1 wherein said spacer sequence is between about 10 bp to 10 kb in length.

3. The cell according to claim 1 wherein said spacer sequence is between 100 bp to 3.8 kb in length.

4. The cell according to claim 1 wherein said spacer sequence is about 500 bp in length.

5. The cell according to claim 1 wherein said spacer sequence is a random sequence of nucleotides.

6. The cell according to claim 1 wherein said spacer sequence encodes a gene product.

7. The cell according to claim 1 wherein said first nucleic acid molecule is a plasmid.

8. The cell according to claim 1 wherein said first nucleic acid molecule is a recombinant virus.

9. The cell according to claim 1 wherein said first nucleic acid molecule is present in said cell as an episome.

10. The cell according to claim 1 wherein said first nucleic acid molecule is integrated into the chromosome of said cell.

11. The cell according to claim 1 wherein said promoter is AAV type 2 P5 promoter.

12. The cell according to claim 1 wherein said parvovirus P5 promoter is from a strain of AAV selected from the group consisting of AAV type 1, AAV type 3, AAV type 4, AAV type5, parvovirus type H1, MVM, and LuIII.

13. The cell according to claim 1 wherein said second nucleic acid molecule is a plasmid.

14. The cell according to claim 1 wherein said second nucleic acid molecule is a recombinant virus.

15. The cell according to claim 1 wherein said second nucleic acid molecule is present in said cell as an episome.

16. The cell according to claim 1 wherein said second nucleic acid molecule is integrated into the chromosome of said cell.

17. The cell according to claim 1 wherein said helper functions are provided by a third nucleic acid molecule.

18. The cell according to claim 17 wherein said third nucleic acid molecule is a plasmid.

19. The cell according to claim 17 wherein said third nucleic acid molecule is a recombinant or wild-type virus.

20. The cell according to claim 17 wherein said third nucleic acid molecule is present in said cell as an episome.

21. The cell according to claim 17 wherein said third nucleic acid molecule is integrated into the chromosome of said cell.

22. The cell according to claim 1 which is derived from a HEK 293 cell.

23. A nucleic acid molecule comprising from 5' to 3': a parvovirus P5 promoter, a spacer, an AAV rep gene sequence comprising a start site and encoding rep 78, rep 68, and other rep gene products, and an AAV cap gene sequence, wherein said spacer consists of sequence heterologous to said promoter and the AAV rep gene sequence, is upstream of the AAV rep start site, and is of sufficient size to reduce expression of the rep78 and rep68 gene products relative to other rep gene products.

24. The molecule according to claim 23 wherein said spacer sequence is between about 10 bp to 10 kb in length.

25. The molecule according to claim 23 wherein said spacer sequence is between 100 bp to 3.8 kb in length.

26. The molecule according to claim 23 wherein said spacer sequence is about 500 bp in length.

27. The molecule according to claim 23 wherein said spacer sequence is a random sequence of nucleotides.

28. The molecule according to claim 23 wherein said spacer sequence encodes a gene product.

29. The molecule according to claim 23 which is a plasmid.

30. The molecule according to claim 23 which is a recombinant virus.

31. A method for producing recombinant adeno-associated virus (AAV), said method comprising the steps of
   (a) culturing a recombinant host cell containing
      (i) a first nucleic acid molecule comprising from 5' to 3': a parvovirus P5 promoter, a spacer, an AAV rep gene sequence comprising a start site and encoding rep78, rep68, and other rep gene products, and an AAV cap gene sequence, wherein said spacer consists of sequence heterologous to said promoter and the AAV rep gene sequence and said spacer is interposed between said promoter and the start site of the rep gene, such that said spacer is upstream of the AAV rep start site and is of sufficient size to reduce expression of the rep78 and rep68 gene products relative to other rep gene products, and
      (ii) a second nucleic acid molecule comprising a minigene comprising a transgene under the control of regulatory sequences directing expression thereof in a host cell and flanked by AAV inverted terminal repeats (ITRs);
      (iii) an optional third nucleic acid molecule which provides helper functions essential to the replication and packaging of rAAV, which functions are not provided by (i) or (ii) or said host cell; and
   (b) isolating from said cell or cell culture, a recombinant AAV capable of expressing said transgene.

32. A nucleic acid molecule comprising from 5' to 3': a parvovirus P5 promoter, a spacer, an AAV rep gene sequence comprising a start site and encoding rep78, rep68, and other rep gene products, and an AAV cap gene sequence, wherein said spacer is interposed between the promoter and the start site of the rep gene start site, such tat said spacer is located upstream of the AAV rep start site and is about 500 bp in length which reduces expression of the rep78 and rep68 gene products relative to other rep gene products.

33. A nucleic acid molecule comprising from 5' to 3': a parvovirus P5 promoter, a spacer, an AAV rep gene sequence comprising a start site and encoding rep78, rep68, and other rep gene products, and an AAV cap gene sequence, wherein said spacer is a random sequence of nucleotides of sufficient length to reduce expression of the rep78 and rep68 gene products relative to other rep gene products.

34. A recombinant host cell containing a nucleic acid molecule according to claim 32.

35. A recombinant host cell containing a nucleic acid molecule according to claim 33.

36. A recombinant host cell containing
    (a) a first nucleic acid molecule integrated into the chromosome of said cell, said molecule comprising, from 5 to 3', a parvovirus P5 promoter, a spacer, an AAV rep gene sequence comprising a start site and encoding rep78, rep68, and other rep gene products, and an AAV cap gene sequence, wherein said spacer is of sufficient size to reduce expression of the rep78 and rep68 gene products relative to other rep gene products,
    (b) a second nucleic acid molecule comprising a minigene comprising a transgene flanked by AAV inverted terminal repeats (ITRs) and under the control of regulatory sequences directing expression thereof in a host cell; and
    (c) helper functions essential to the replication and packaging of rAAV.

37. A method for producing a recombinant adeno-associated virus (AAV), said method comprising the steps of culturing a host cell according to claim 36 and isolating from said cell or cell culture, a recombinantAAV capable of expressing said transgene.

38. A recombinant virus comprising from 5' to 3': a parvovirus P5 promotor, a spacer, an AAV rep gene sequence comprising a start site and encoding rep 78, rep 68, and other rep gene products, and an AAV cap gene sequence, wherein said spacer is upstream of the AAV rep start site and is of sufficient size to reduce expression of the rep78 and rep68 gene products relative to other rep gene products.

39. The recombinant virus according to claim 38 wherein said spacer sequence is between about 10 bp to 10 kb in length.

40. The recombinant virus according to claim 38 wherein said spacer sequence is between 100 bp to 3.8 kb in length.

41. The recombinant virus according to claim 38 wherein said spacer sequence is about 500 bp in length.

42. The recombinant virus according to claim 38 wherein said spacer sequence is a random sequence of nucleotides.

43. The recombinant virus according to claim 38 wherein said spacer sequence encodes a gene product.

44. The recombinant virus according to claim 38 wherein said recombinant virus is an adenovirus or a baculovirus.

45. The recombinant virus according to claim 38 wherein said promoter is AAV type 2 P5 promoter.

46. The recombinant virus according to claim 38 wherein said parvovirus P5 promoter is from the group consisting of LuIII, MVM, parvovirus type H1, AAV type 1, AAV type 3, AAV type 4, and AAV type 5.

47. A recombinant host cell containing a recombinant virus according to claim 38.

48. A method for producing recombinant adeno-associated virus (AAV), said method comprising the steps of
    (a) culturing a recombinant host cell according to claim 47 which further comprises:
        (i) a nucleic acid molecule comprising a minigene comprising a transgene flanked by AAV inverted terminal repeats (ITRs) and under the control of regulatory sequences directing expression thereof in a host cell and
        (ii) helper functions essential to the replication and packaging of rAAV; and
    (b) isolating from said cell or cell culture, a recombinant AAV capable of expressing said transgene.

49. The method according to claim 48 wherein said nucleic acid molecule is a plasmid.

50. The method according to claim 48 wherein said nucleic acid molecule is present in said cell as an episome.

51. The method according to claim 48 wherein said nucleic acid molecule is integrated into the chromosome of said cell.

52. The method according to claim 48 wherein said helper functions are provided by a second nucleic acid molecule.

53. The method according to claim 52 wherein said second nucleic acid molecule is a plasmid.

54. The method according to claim 52 wherein said second nucleic acid molecule is a recombinant or wild-type virus.

55. The method according to claim 52 wherein said second nucleic acid molecule is present in said cell as an episome.

56. The method according to claim 52 wherein said second nucleic acid molecule is integrated into the chromosome of said cell.

* * * * *